(12) United States Patent
Kim et al.

(10) Patent No.: US 11,607,433 B2
(45) Date of Patent: Mar. 21, 2023

(54) **COMPOSITION FOR PREVENTING, IMPROVING, OR TREATING AUTISM SPECTRUM DISORDERS INCLUDING *AGATHOBACULUM* SP. STRAIN AS ACTIVE INGREDIENT**

(71) Applicant: HEALTHBIOME, Daejeon (KR)

(72) Inventors: Byoung Chan Kim, Daejeon (KR); Kyoung Shim Kim, Daejeon (KR); Chul Ho Lee, Daejeon (KR); Dong Ho Chang, Daejeon (KR); Yong-Hoon Kim, Daejeon (KR); Jung-Ran Noh, Daejeon (KR); Dong Hui Choi, Daejeon (KR); Jung Hwan Hwang, Daejeon (KR); Jun Go, Daejeon (KR); Jaehun Kim, Daejeon (KR); Hye-Yeon Park, Daejeon (KR); Yun-Jung Seo, Daejeon (KR); Young-Kyoung Ryu, Daejeon (KR); In-Bok Lee, Daejeon (KR); Young Keun Choi, Daejeon (KR); Jung-Hyeon Choi, Daejeon (KR)

(73) Assignee: HEALTHBIOME, Daejeon (KR)

( * ) Notice: Subject to any disclaimer, the term of this patent is extended or adjusted under 35 U.S.C. 154(b) by 0 days.

(21) Appl. No.: 16/772,255

(22) PCT Filed: Dec. 12, 2018

(86) PCT No.: PCT/KR2018/015755
§ 371 (c)(1),
(2) Date: Jun. 12, 2020

(87) PCT Pub. No.: WO2019/117616
PCT Pub. Date: Jun. 20, 2019

(65) Prior Publication Data
US 2021/0093678 A1    Apr. 1, 2021

(30) Foreign Application Priority Data

Dec. 12, 2017 (KR) ........................ 10-2017-0170076

(51) Int. Cl.
*A61K 35/74* (2015.01)
*A61P 25/00* (2006.01)

(52) U.S. Cl.
CPC .............. *A61K 35/74* (2013.01); *A61P 25/00* (2018.01)

(58) Field of Classification Search
CPC ................................ A61K 35/74; A61P 25/10
See application file for complete search history.

(56) References Cited

U.S. PATENT DOCUMENTS

2019/0300972 A1* 10/2019 Kim ....................... C12N 1/205

FOREIGN PATENT DOCUMENTS

| JP | 2016-084352 | 5/2016 |
| KR | 10-2004-0074053 | 8/2004 |
| KR | 10-2017-0086492 | 7/2017 |
| KR | 10-2017-0118828 | 10/2017 |
| KR | 10-1799830 | 11/2017 |
| WO | WO 2011/044516 A2 | 4/2011 |
| WO | WO 2013/037068 A1 | 3/2013 |
| WO | WO 2016/133450 A1 | 8/2016 |

OTHER PUBLICATIONS

Sharon Ahn et al., "*Agathobaculum butyriciproducens* gen. nov. sp. nov., a strict anaerobic, butyrate-producing gut bacterium isolated from human faeces and reclassification of *Eubacterium desmolans* as *Agathobaculum desmolans* comb. nov.", International Journal of Systematic and Evolutionary Microbiology, 66, 3656-3661, Sep. 1, 2016.
Nicholas M. Vogt et al., "Gut microbiome alterations in Alzheimer's disease", Scientific Reports 7, Article No. 13537, Oct. 19, 2017.
Young Shin Kim et al., "Prevalence o f Autism Spectrum Disorders in a Total Population Sample", Am J Psychiatry 168:904-912, Sep. 1, 2011.
*Eubacterium* sp. SR79 16S ribosomal RNA gene, partial sequence GenBank:KP889099.2; Jan. 6, 2016; (2 pages in English).
*Agathobaculum butyriciproducens* strain SR79 16S ribosomal RNA gene, partial sequence GenBank:KP889099.2;, Oct. 31, 2017; (2 pages in English).

* cited by examiner

*Primary Examiner* — Robert A Zeman
(74) *Attorney, Agent, or Firm* — NSIP Law

(57) ABSTRACT

The present invention relates to an *Agathobaculum* sp. strain having prophylactic or therapeutic effects on autism spectrum disorders, and use thereof. When the intestinal microorganism *Agathobaculum* sp. strain of the present invention was orally administered to valproic acid (VPA)-induced autism model mice and BTBR autism model mice, the effects of remarkably improving autism spectrum disorders including repetitive behaviors, hyperactivity, social deficiency and cognitive/memory dysfunction of the mice were observed, as compared with a non-treated control. Accordingly, it may be usefully applied to foods, drugs, or feeds for preventing or treating autism spectrum disorders, and thus is very useful in the relevant industries.

5 Claims, 3 Drawing Sheets

[FIG. 1]
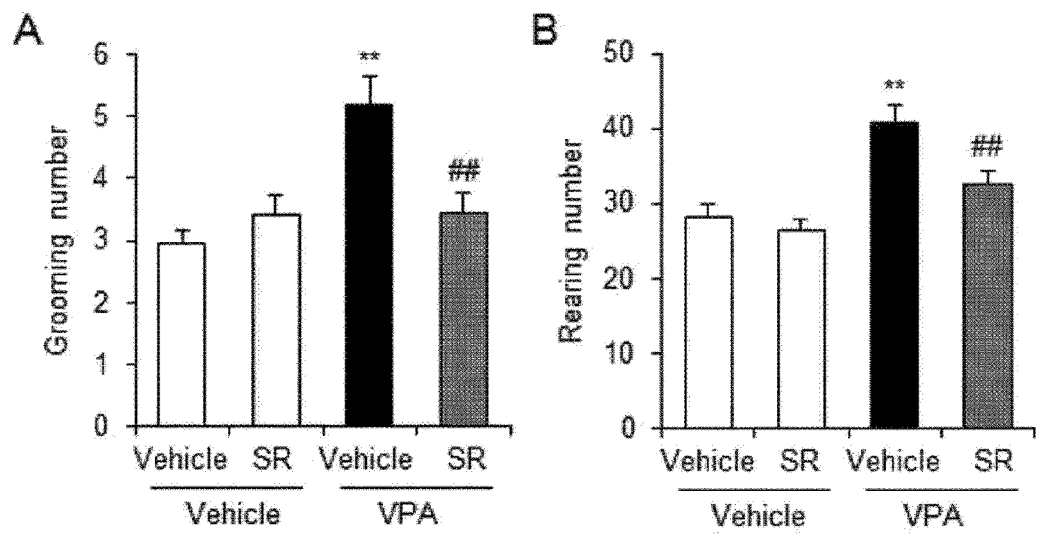
[FIG. 2]
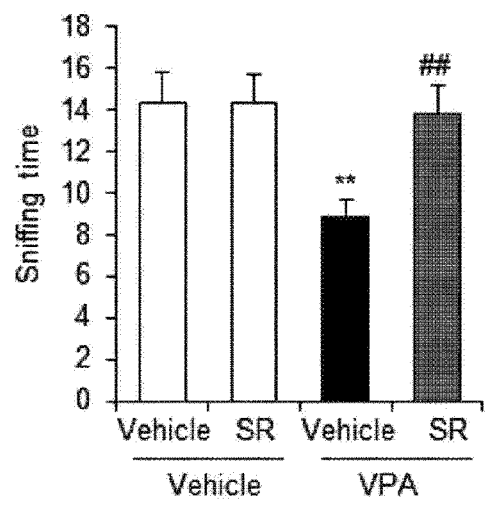

[FIG. 3]
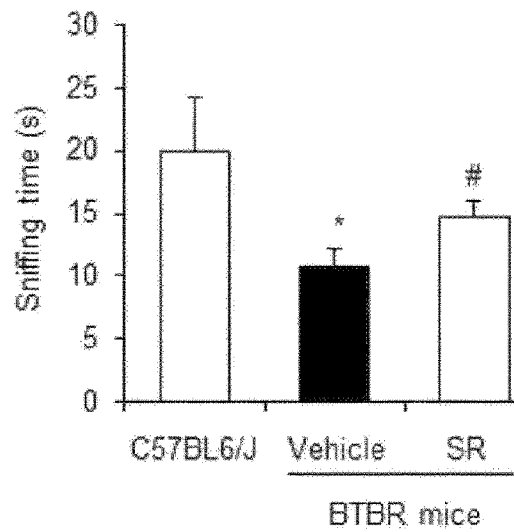
[FIG. 4]
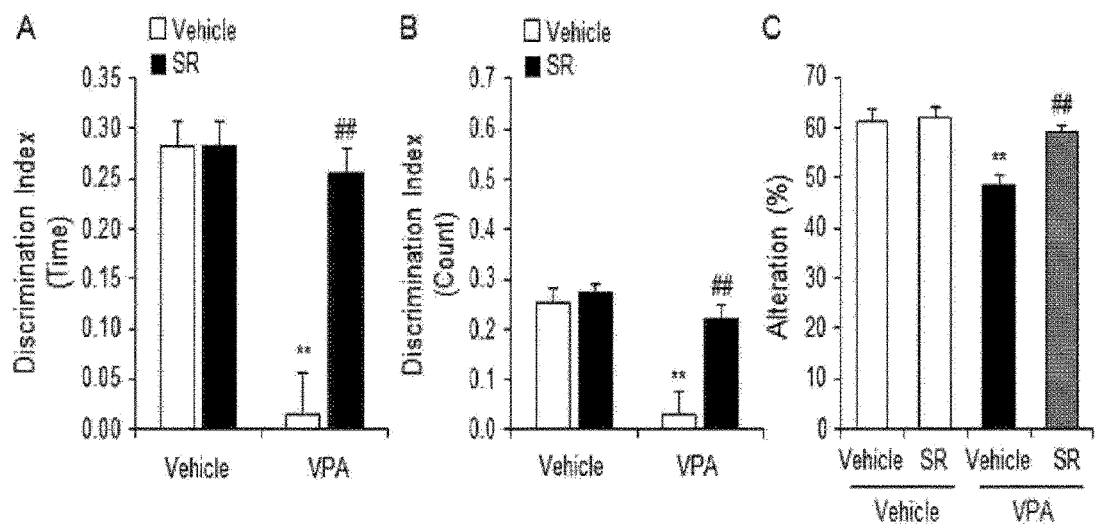

[FIG. 5]
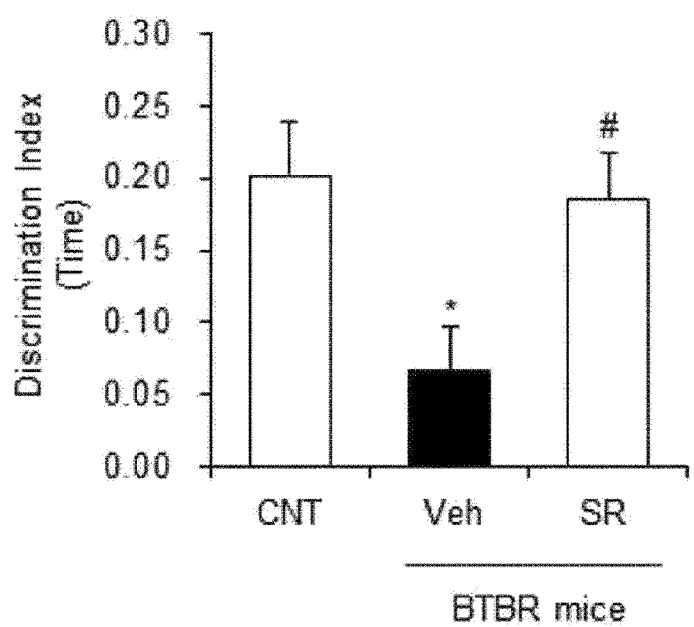

COMPOSITION FOR PREVENTING, IMPROVING, OR TREATING AUTISM SPECTRUM DISORDERS INCLUDING *AGATHOBACULUM* SP. STRAIN AS ACTIVE INGREDIENT

TECHNICAL FIELD

The present invention relates to a composition for preventing, improving, or treating autism spectrum disorders, the composition including an *Agathobaculum* sp. strain as an active ingredient.

BACKGROUND ART

Autism is a brain developmental disorder, the main symptoms of which is disability of social interaction, stereotyped behaviors and restricted interests, and impaired verbal and non-verbal communication. Autism is a disease that usually starts and is diagnosed under 3 years of age and affects a wide range of developmental stages, and the impairments usually continue throughout one's lifetime, causing extreme pain to patients and their families, and the disease requires quite high medical and social costs. In recent years, with emphasizing that the degree and prognosis of autism is very diverse, the term "autism" used in the past is modified to autism spectrum disorder (ASD). Autism spectrum disorders (ASD) includes autism as well as pervasive developmental disorder (PDD) including Asperger's syndrome, Rett's disorder, childhood disintegrative disorder, and pervasive developmental disorder—not otherwise specified (PDD NOS), etc.

Autism is a disease, the prevalence of which has rapidly increased over the last 20 years. According to the reports by the U.S. Centers for Disease Control and Prevention (CDC) in 2012, the prevalence of autism was estimated to be over 1 in 100 children. In particular, epidemiological studies on Korean children have reported a very high prevalence, in which 2.64% of children aged 7 to 12 years have autism or other autism spectrum disorders (Kim et al., Am J Psychiatry 2011 168:904-912).

Recent studies have revealed that intestinal microorganisms actively influence the control of brain function and the onset of brain diseases as well as the intestinal health and intestinal diseases in humans. However, there have been no reports of prophylactic or therapeutic effects of a novel intestinal microorganism *Agathobaculum butyriciproducens* SR79 strain on autism spectrum disorders.

Meanwhile, Korean Patent Publication No. 2004-0074053 discloses 'a novel strain of lactic acid bacterium, and an edible composition, a drug, and a veterinary product, each including the same', and Korean Patent Publication No. 2017-0086492 discloses 'a composition and a method including bacteria for improving behaviors in neurodevelopmental disorders'. However, there have been no reports of 'an *Agathobaculum* sp. strain having a prophylactic or therapeutic effect on autism spectrum disorders, and use thereof', as in the present invention.

DISCLOSURE

Technical Problem

The present invention has been made in view of the above-described needs, and it was confirmed that when the *Agathobaculum* sp. strain isolated in the present invention was orally administered to valproic acid (VPA)-induced autism model mice, autism spectrum disorders including repetitive behaviors, hyperactivity, social deficiency, and cognitive/memory dysfunction of the mice were remarkably improved, as compared with a non-treated control, thereby completing the present invention.

Technical Solution

In order to solve the above objects, the present invention provides a pharmaceutical composition for preventing or treating autism spectrum disorders, the pharmaceutical composition including, as an active ingredient, one or more selected from the group consisting of an *Agathobaculum* sp. strain, vesicle derived from the strain, a culture of the strain, a concentrate of the culture, a dry product of the culture, and an extract of the culture.

Further, the present invention provides a health functional food composition for preventing or improving autism spectrum disorders, the health functional food composition including, as an active ingredient, one or more selected from the group consisting of an *Agathobaculum* sp. strain, vesicle derived from the strain, a culture of the strain, a concentrate of the culture, a dry product of the culture, and an extract of the culture.

Further, the present invention provides a feed additive composition for preventing or improving autism spectrum disorders, the feed additive composition including, as an active ingredient, one or more selected from the group consisting of an *Agathobaculum* sp. strain, vesicle derived from the strain, a culture of the strain, a concentrate of the culture, a dry product of the culture, and an extract of the culture.

Further, the present invention provides a veterinary drug composition for preventing or treating autism spectrum disorders, the veterinary drug composition including, as an active ingredient, one or more selected from the group consisting of an *Agathobaculum* sp. strain, vesicle derived from the strain, a culture of the strain, a concentrate of the culture, a dry product of the culture, and an extract of the culture.

Advantageous Effects

When the intestinal microorganism of the present invention (i.e., the *Agathobaculum* sp. strain) was orally administered to valproic acid (VPA)-induced autism model mice and BTBR autism model mice, the effects of remarkably improving autism spectrum disorders including repetitive behaviors, hyperactivity, social deficiency, and cognitive/memory dysfunction of the mice were observed, as compared with a non-treated control. Accordingly, it may be usefully applied to foods, drugs, or feeds for preventing or treating autism spectrum disorders, and thus is very useful in the relevant industries.

BRIEF DESCRIPTION OF DRAWINGS

FIG. 1 shows results of analyzing repetitive behaviors (A) and hyperactivity behaviors (B) of model mice according to treatment with an *Agathobaculum* sp. SR79 strain isolated in the present invention, in which VPA represents valproic acid treatment, Vehicle represents a non-treated control, and SR represents *Agathobaculum* sp. SR79 strain treatment.

FIG. 2 shows the time measured by observing interactions (sniffing behaviors) with other mice, which was measured in order to investigate the effect of improving social behaviors of model mice according to treatment with the *Agathobaculum* sp. SR79 strain isolated in the present invention.

FIG. 3 shows the time measured by observing interactions (sniffing behaviors) with other mice, which was measured in BTBR mice in order to investigate the effect of improving social behaviors of model mice according to treatment with the *Agathobaculum* sp. SR79 strain isolated in the present invention.

FIG. 4 shows results of testing the effect of improving cognitive functions of model mice according to treatment with the *Agathobaculum* sp. SR79 strain isolated in the present invention (A: new object exploration time; B: new object exploration count; C: a percentage of alternation entering a new space in a Y-maze alternation test for the working behaviors of the mice).

FIG. 5 shows results of testing the effect of improving cognitive functions of BTBR mice according to treatment with the *Agathobaculum* sp. SR79 strain isolated in the present invention, which was tested by measuring the time spent in exploring a new object.

BEST MODE FOR CARRYING OUT THE INVENTION

In order to achieve the objects of the present invention, the present invention provides a pharmaceutical composition for preventing or treating autism spectrum disorders, the pharmaceutical composition including, as an active ingredient, one or more selected from the group consisting of an *Agathobaculum* sp. strain, vesicle derived from the strain, a culture of the strain, a concentrate of the culture, a dry product of the culture, and an extract of the culture.

In the strain according to one embodiment of the present invention, the *Agathobaculum* sp. strain may be *Agathobaculum butyriciproducens*, and preferably the *Agathobaculum butyriciproducens* may be an *Agathobaculum butyriciproducens* SR79 strain with Accession No. KCTC 13036BP, but these are not limited thereto.

The *Agathobaculum butyriciproducens* SR79 strain according to the present invention is an absolute anaerobic microorganism isolated by the present inventors directly from the intestine of a healthy Korean, and it was confirmed by molecular biological, physiological/biochemical microbiological identification methods that the strain is a novel microorganism belonging to a novel genus and species different from the standard strain previously reported. The name of the microorganism had been suggested as *Agathobaculum butyriciproducens* SR79. The SR79 strain identified in the present invention was accepted by the International Journal of Systematic and Evolutionary Microbiology as a standard strain for the genus and species of *Agathobaculum butyriciproducens*, which is the new scientific name proposed by the present inventors.

Further, the *Agathobaculum butyriciproducens* SR79 strain was deposited in the Korean Collection of Type Cultures on Jun. 7, 2016, under Accession Number KCTC 13036BP.

Use of the novel isolated microorganism, i.e., the *Agathobaculum butyriciproducens* SR79 strain, for the prevention or treatment of autism spectrum disorder-related diseases has never been disclosed, and the present inventors demonstrated for the first time that this strain may be used for the prevention or treatment of autism spectrum disorder-related diseases.

In the present invention, it was confirmed that oral administration of the SR79 strain exhibits efficacy of remarkably improving repetitive behaviors (FIG. 1A) and hyperactivity (FIG. 1B), social deficiency (FIGS. 2 and 3), and cognitive/memory dysfunction (FIGS. 4 and 5) in valproic acid-induced mouse models showing autism spectrum disorders and attention deficit hyperactivity disorder-related behavioral phenotypes. Based on these results, it was confirmed that the SR79 strain has the effects of preventing and treating neurodevelopmental disorders such as autism spectrum disorders, attention deficit hyperactivity disorders, etc.

The "autism spectrum disorders" of the present invention includes autism as well as pervasive developmental disorder (PDD) including Asperger's syndrome, Rett's disorder, childhood disintegrative disorder, and pervasive developmental disorder—not otherwise specified (PDD NOS), etc. Generally, any symptoms that are reported as symptoms of autism spectrum disorders may be included, and preferably, any one or more symptoms selected from the group consisting of hyperactivity symptoms, social deficiency symptoms, cognitive/memory dysfunction behaviors, and epileptic seizure symptoms may be included, but are not limited thereto.

As used herein, the term "prevention" refers to all of the actions by which the occurrence of autism spectrum disorders is restrained or retarded by administration of the pharmaceutical composition according to the present invention, and the term "treatment" refers to all of the actions by which symptoms of a subject having or suspected of having the autism spectrum disorders have taken a turn for the better or have been modified favorably by administration of the pharmaceutical composition.

The pharmaceutical composition of the present invention may further include an appropriate carrier, excipient, and diluent commonly used in the preparation of pharmaceutical compositions.

The pharmaceutical composition according to the present invention may be formulated, according to a common method, into oral dosage forms such as powders, granules, tablets, capsules, suspensions, emulsions, syrups, aerosols, etc., external dosage forms, suppository, or sterile injectable solution. The carrier, excipient, and diluent which may be included in the pharmaceutical composition according to the present invention may include various compounds or mixtures, including lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc. Upon formulation, the pharmaceutical composition may be prepared using a commonly used diluent or excipient, such as a filler, an extender, a binder, a humectant, a disintegrant, a surfactant, etc. A solid formulation for oral administration may include a tablet, a pill, a powder, granules, a capsule, etc. Such solid formulations may be prepared by mixing the strain or the vesicle derived from the strain with at least one excipient, for example, starch, calcium carbonate, sucrose or lactose, gelatin, etc. In addition to the simple excipients, a lubricant, such as magnesium stearate or talc, may be used. A liquid formulation for oral administration may include a suspension, a solution for internal use, an emulsion, a syrup, etc. In addition to a simple diluent commonly used, such as water and liquid paraffin, the formulation may include various excipients such as a humectant, a sweetener, an aromatic, a preservative, etc. A formulation for parenteral administration may include a sterilized aqueous solution, a non-aqueous solvent, a suspension, an emulsion, a lyophilized formulation, and a suppository. The non-aqueous solvent and the suspension may include propylene glycol, polyethylene glycol, a vegetable oil such as olive oil, an injectable ester such as ethyl oleate, etc. As a base of the suppository, witepsol, macrogol, Tween 61, cocoa butter, laurin butter, glycerogelatin, etc. may be used.

The pharmaceutical composition of the present invention may be administered in a pharmaceutically effective amount. As used herein, the phrase "pharmaceutically effective amount" means a sufficient amount to prevent or treat a disease at a reasonable benefit/risk ratio applicable to any medical prevention or treatment, and an effective dose level may be determined by factors including severity of a disease, drug activity, a patient's age, body weight, health conditions, sex, and sensitivity to drugs, administration time and route of the composition of the present invention, an excretion rate, a treatment period, drugs used along with or concurrently used with the composition of the present invention, and other factors well known in the medical field. The pharmaceutical composition of the present invention may be administered as an individual therapeutic agent or in combination with other therapeutic agents sequentially or simultaneously once or multiple times. It is important to administer a minimum amount that may achieve the maximum effect without adverse effects, considering all the factors described above.

With regard to the administration dose of the pharmaceutical composition of the present invention, the pharmaceutical composition of the present invention may be, for example, administered to a mammal including a human in a daily dose of $1.0 \times 10^9$ CFU, but is not limited thereto. The administration frequency of the composition of the present invention may be, but is not particularly limited to, administered once a day or several times in divided doses a day. The above administration dose does not limit the scope of the present invention in any aspect.

In another aspect to achieve the above objects, the present invention provides a method of preventing or treating autism spectrum disorders, the method including the step of administering a pharmaceutically effective amount of the pharmaceutical composition to a subject having autism spectrum disorders or at risk of having autism spectrum disorders.

As described above, one or more selected from the group consisting of the intestinal microorganism SR79 strain provided in the present invention, vesicle derived from the strain, a culture of the strain, a concentrate of the culture, a dry product of the culture, and an extract of the culture may be used as an active ingredient of the pharmaceutical composition for preventing or treating autism spectrum disorders, and therefore, the composition may be used in preventing or treating autism spectrum disorders.

As used herein, the term "subject" may include, without limitation, mammalian animals including mice, livestock, humans, etc. having autism spectrum disorders or at risk of having autism spectrum disorders.

In the method of the present invention for treating autism spectrum disorders, the pharmaceutical composition may be administered via any of the common routes, as long as it may reach desired tissue. The pharmaceutical composition of the present invention may be, but is not particularly limited to, administered orally or intrarectally, and on occasion, may be administered via other routes according to the desired purpose. However, since the intestinal SR79 strain may be denatured by gastric acid upon oral administration, the active ingredient of the composition for oral administration should be coated or formulated for protection against degradation in the stomach. In addition, the composition may be administered using a certain apparatus capable of transporting the active ingredient into a target cell.

Further, the present invention provides a health functional food composition for preventing or improving autism spectrum disorders, the health functional food composition including, as an active ingredient, one or more selected from the group consisting of the strain, vesicle derived from the strain, a culture of the strain, a concentrate of the culture, a dry product of the culture, and an extract of the culture.

In the health functional food composition according to one embodiment of the present invention, the *Agathobaculum* sp. strain may be *Agathobaculum butyriciproducens*, and preferably, the *Agathobaculum butyriciproducens* may be an *Agathobaculum butyriciproducens* SR79 strain with Accession No. KCTC 13036BP, but these are not limited thereto.

In the health functional food composition according to one embodiment of the present invention, the "autism spectrum disorders" includes autism as well as pervasive developmental disorder (PDD) including Asperger's syndrome, Rett's disorder, childhood disintegrative disorder, and pervasive developmental disorder—not otherwise specified (PDD NOS), etc. Generally, any symptoms that are reported as symptoms of autism spectrum disorders may be included, and preferably, any one or more symptoms selected from the group consisting of hyperactivity symptoms, social deficiency symptoms, cognitive/memory dysfunction behaviors, and epileptic seizure symptoms may be included, but are not limited thereto.

The strain is the same as described above, and may be added to health functional foods for the purpose of preventing or improving autism spectrum disorders.

When the above-mentioned strain of the present invention or the culture thereof, etc. is used as the health functional food composition, the strain or the culture thereof may be added as it is or used along with other foods or food components, and may be appropriately used according to a common method. A mixing amount of the active ingredients may be appropriately determined according to the intended use (prevention, health, or therapeutic treatment).

The food (or health functional food) of the present invention may further include sitologically acceptable components, which are commonly added during the preparation of foods. Preferably, in addition to the above-mentioned active ingredients, the health food composition may further include one or more selected from nutrients, vitamins, electrolytes, a flavoring agent, a colorant, a thickening agent, pectic acid and a salt thereof, alginic acid and a salt thereof, organic acids, a protective colloidal thickening agent, a pH adjusting agent, a stabilizer, a preservative, glycerin, alcohols, and carbonating agents used in carbonated beverages, but is not limited thereto. For example, when the food is prepared as a drink, it may further include, in addition to the strain of the present invention, one or more components of citric acid, liquid fructose, sugar, glucose, acetic acid, malic acid, fruit juice, etc.

The amount that can be included in the active ingredient of the food (or health functional food) according to the present invention may be appropriately selected according to age, sex, body weight, conditions, and disease symptoms of a person who needs the food for preventing or improving autism spectrum disorders, and preferably, the active ingredient may be used in a daily dose of about 0.01 g to about 10.0 g per an adult. By ingesting the food having such content, the effect of preventing or improving autism spectrum disorders may be obtained.

Further, the present invention provides a method of preparing a microbial formulation for preventing or treating autism spectrum disorders, the method including the step of culturing the strain.

The method of culturing the strain of the present invention may be carried out according to a method commonly used in the art.

The microbial formulation of the present invention for preventing or treating autism spectrum disorders may be prepared using, as an active ingredient, an *Agathobaculum* sp. strain, preferably, *Agathobaculum butyriciproducens*, and most preferably *Agathobaculum butyriciproducens* SR79 strain with Accession No. KCTC 13036BP. The microbial formulation for preventing or treating autism spectrum disorders according to the present invention may be prepared as a solution, a powder, a suspension, a dispersion, an emulsion, an oil dispersion, a paste, a dust, a propellant, or granules, but is not limited thereto.

In still another aspect, the present invention provides a feed additive composition for preventing or improving autism spectrum disorders, the composition including, as an active ingredient, one or more selected from the group consisting of the strain, vesicle derived from the strain, a culture of the strain, a concentrate of the culture, a dry product of the culture, and an extract of the culture.

The strain is the same as described above, and may be added as the feed additive composition for the purpose of preventing or improving autism spectrum disorders. The feed additive of the present invention corresponds to a supplementary feed according to Control of Livestock and Fish Feed Act.

As used herein, the term "feed" refers to any natural or artificial diet, meal, etc., or components of such meal intended or suitable to be eaten, taken in, or digested by animals. A kind of the feed is not particularly limited, and any feed generally used in the art may be used. Non-limiting examples of the feed may include plant-based feeds, such as grains, nuts, food by-products, seaweeds, fibers, drug by-products, fats and oils, starches, meals, or grain by-products, etc.; and animal-based feeds such as proteins, inorganic matters, fats and oils, minerals, fats and oils, single cell proteins, zooplanktons, or foods, etc. These may be used alone or in a mixture of two or more thereof.

Further, the present invention provides a veterinary drug composition for preventing or treating autism spectrum disorders, the veterinary drug composition including, as an active ingredient, one or more selected from the group consisting of an *Agathobaculum* sp. strain, vesicle derived from the strain, a culture of the strain, a concentrate of the culture, a dry product of the culture, and an extract of the culture.

The composition may be preferably achieved by having the effect of preventing or treating autism spectrum disorders, which is the same as described above.

When the composition of the resent invention is used as the veterinary drug composition, the composition may be used as it is or used along with other drug or quasi-drug components, and may be appropriately used according to a common method, but is not limited thereto. A mixing amount of the active ingredients may be appropriately determined according to the intended use (prevention, health, improvement, or therapeutic treatment).

DETAILED DESCRIPTION OF THE INVENTION

Hereinafter, the construction and effects of the present invention will be described in more detail with reference to Examples. However, these Examples are only for illustrating the present invention, and the scope of the present invention is not intended to be limited by these Examples.

Animal Model and Administration of SR79 Strain

C57BL6/J mice were used as experimental animals. From 3 weeks of age, autism model male mice born by administering VPA to pregnant mice were orally administered with an intestinal microorganism SR79 strain in a concentration of $1.0 \times 10^9$ CFU daily. From 4 weeks after microbial administration, the effects of microbial administration were examined by performing a behavioral test for neurodevelopmental disorders of mice. Herein, a control group (vehicle) was orally administered with 25% glycerol/PBS in the same volume as SR79.

Further, a male inbred BTBR T+tf/J (BTBR) mouse model used worldwide was used as an autism spectrum disorder animal model. From 3 weeks of age, the mice were orally administered with the intestinal microorganism SR79 strain in a concentration of $1.0 \times 10^9$ CFU daily. From 4 weeks after microbial administration, the effects of microbial administration were examined by performing a behavioral test for neurodevelopmental disorders of mice. Herein, a control group (vehicle) was orally administered with 25% glycerol/PBS in the same volume as SR79. At this time, the control mouse was C57BL6/J male mouse at the same age.

Example 1. Test of Repetitive Behaviors and Hyperactivity of Mouse

FIG. 1 shows results of analyzing repetitive behaviors (A) and hyperactivity behaviors (B) of mice. VPA-administered mice showed a statistically significant increase in the number of repetitive grooming behaviors. In contrast, when VPA-administered mice were ingested with the SR79 strain, repetitive behaviors were remarkably reduced (A, ##$p<0.01$). Additionally, in the results of analyzing the hyperactivity behaviors of mice through analysis of rearing behaviors of mice, it was also confirmed that hyperactivity behaviors occurring in the VPA-administered mice were significantly reduced by SR79 administration (B, ##$p<0.01$).

Example 2. Test of Social Behaviors of Mouse

FIG. 2 shows the time measured by observing interactions (sniffing behaviors) with other mice, which was measured in order to test social behaviors of mice. The reduced social behaviors of the VPA-administered mice were significantly increased by SR79 administration (##$p<0.01$).

Further, FIG. 3 shows the time measured by observing interactions (sniffing behaviors) with other mice, which was measured in BTBR mice in order to test social behaviors of the mice. Their interactions (sniffing behaviors) which were reduced as compared with control C57BL6/J mice were significantly increased by SR79 administration (#$p<0.05$).

Example 3. Test of Cognitive Memory of Mouse

FIG. 4 shows the effect of improving cognitive functions of mice, which was tested by a novel object recognition test for investigating the cognitive memory for a new object when the new object was provided along with the previously explored object. It was confirmed that the cognitive learning memory for the new object was remarkably reduced in the VPA-administered mice, and the cognitive learning memory was significantly improved by SR79 administration (A: new object exploration time; B: new object exploration count; ##$p<0.01$). In addition, as a result of measuring a percentage of alternation entering a new space in a Y-maze alternation test for the working behaviors of the mice (FIG. 4C), it was observed that the reduced working memory by VPA administration was significantly increased by SR79 administration (#$p<0.05$). Further, FIG. 5 shows the effect of improving cognitive functions of BTBR mice, which was tested by measuring the time spent in exploring a new object. Significant improvement was observed by SR79 administration.

The invention claimed is:

1. A method for treating autism spectrum disorders, comprising a step of administering pharmaceutical composition comprising, as an active ingredient, an *Agathobaculum* sp. strain,
    wherein the *Agathobaculum* sp. strain is an *Agathobaculum butyriciproducens* SR79 strain with Accession No. KCTC 13036BP.

2. The method of claim 1, wherein the autism spectrum disorders are characterized by repetitive behaviors, hyperactivity, social deficiency, or cognitive/memory dysfunction behaviors.

3. A method for improving autism spectrum disorders, comprising a step of administering health functional food composition comprising, as an active ingredient, an *Agathobaculum* sp. strain,
    wherein the *Agathobaculum* sp. strain is an *Agathobaculum butyriciproducens* SR79 strain with Accession No. KCTC 13036BP.

4. A method for improving autism spectrum disorders, comprising a step of administering feed additive composition comprising, as an active ingredient, an *Agathobaculum* sp. strain,
    wherein the *Agathobaculum* sp. strain is an *Agathobaculum butyriciproducens* SR79 strain with Accession No. KCTC 13036BP.

5. A method for treating autism spectrum disorders, comprising a step of administering veterinary drug composition comprising, as an active ingredient, an *Agathobaculum* sp. strain,
    wherein the *Agathobaculum* sp. strain is an *Agathobaculum butyriciproducens* SR79 strain with Accession No. KCTC 13036BP.

* * * * *